United States Patent [19]

Inoue et al.

[11] Patent Number: 4,773,427

[45] Date of Patent: Sep. 27, 1988

[54] WATER-PROOF DEVICE FOR TRANSMITTER

[75] Inventors: Hirokatsu Inoue, Chiba; Chuji Shimizu, Funabashi, both of Japan

[73] Assignee: Fukuda Denshi Co., Ltd., Tokyo, Japan

[21] Appl. No.: 53,783

[22] Filed: May 26, 1987

[51] Int. Cl.$^4$ .............................................. A45C 11/00
[52] U.S. Cl. .................... 128/696; 128/644; 128/903; 128/695
[58] Field of Search ............... 128/696, 644, 903, 695, 128/419 P

[56] References Cited

U.S. PATENT DOCUMENTS 4,069,955  1/1978  Noyes ................................. 128/903
4,495,917  1/1985  Byers .................................. 128/903
4,681,118  7/1987  Asai et al. .......................... 128/903
4,686,998  8/1987  Robbins .............................. 128/903

Primary Examiner—William E. Kamm
Assistant Examiner—Timothy Keegan
Attorney, Agent, or Firm—Pollock, VandeSande & Priddy

[57] ABSTRACT

A water-proof device for a transmitter is disclosed which comprises a plurality of water-proof electrodes attached to the surface of a man for deriving minute electrocardiogram signals. A water-proof plug receives a plurality of electrode leads and, a connector for connects the leads to, a transmitter. The transmitter and connector are accommodated in a sealed water-proof sack.

1 Claim, 3 Drawing Sheets

WATER-PROOF DEVICE FOR TRANSMITTER

BACKGROUND OF THE INVENTION

1. Field of the Invention

This invention relates to a water-proof device for an electrocardiograph transmitter used for recording an electrocardiogram in order to learn the condition of the heart of a man exercising underwater, such as swimming or underwater rehabilitation.

2. Prior Art

As a result of the recent development of the medical technology and improvement of the general diagnosis and treatment levels concerning the heart, many heavy and light heart disease patients have been found, thus contributing to the therapy of heart diseases.

However, light heart disease patients and also school children suffering from heart diseases found in nationwide heart conducted in schools are inhibited from receiving lessons in swimming which is a hard physical exercise.

In the infant's cardiology so far, the basis, on which a decision that a school child suffering from a light heart disease can safely exercise swimming is made, is constituted by the results of study of an electrocardiogram of the child on the ground and not while swimming.

However, the status of the circulatory system of a man during swimming is peculiarly different from the motion on the ground, and the status of the circulatory system of a school child during swimming has not been accurately analyzed. Therefore, the safety of a school child suffering from a heart disease during swimming cannot be confirmed. Therefore, it has been difficult to allow the swimming of a child suffering from a light heart disease, who is thought as a result of the conventional heart examination that he or she can safety exercise swimming.

For the above reason, it has become an urgent necessity to verify that the swimming of the child as noted above is safe in view of his or her electrocardiograph during swimming.

In order to record an electrocardiogram of a man during swimming, it is necessary to attach electrodes to the skin, connect these electrodes to an electrocardiograph installed on the ground through a cable, let the man with the electrodes swim and detect a minute current from the heart as induced on the skin during the swimming with the electrocardiograph installed on the ground through the cable, thus measuring a change in the potential generated in the man with the electrocardiograph.

When recording the electrocardiograph of the man during swimming with the electrocardiograph installed on the ground, a long cable is required if the man is to cover a long distance by swimming. Increasing the cable length, however, leads to increased expenditures for the recording. In addition, when the cable length is increased, the minute signal derived from the heart is liable to be lost before it reaches the electrocardiograph through the cable. In such a case, an accurate electrocardiogram cannot be obtained. Further, when the swimming is done violently, it is liable that the cable entangles on the hands and legs, making the swimming difficult.

To overcome this difficulty, it has been proposed to record by radio an electrocardiographic signal of a man moving in water under remote control.

This method will now be described with reference to FIGS. 3 and 4. Referring to FIG. 3, water-proof electrodes 1 to 3 are attached to the skin of a man. These water-proof electrodes 1 to 3 are connected by leads 4 to 6 to a transmitter 7 which generates a radio signal.

The transmitter 7, to which the water-proof electrodes 1 to 3 are connected through the leads 4 to 6, is installed by a mounting belt 8 on the skin of the swimmer, as shown in FIG. 4. While the swimmer is swimming with the transmitter 7, an electrocardiographic signal is detected by the water-proof electrodes 1 to 3 and supplied through the leads 4 to 6 to the transmitter 7.

The electrocardiographic signal led to the transmitter 7 is transmitted from an antenna 9. The transmitted electrocardiographic signal is intercepted by an antenna 11 of a receiver 10 which is installed on the ground. The received electrocardiographic signal is displayed on a cathode-ray tube 12 or recorded on a recording sheet 13 as an electrocardiograph.

When this method is adopted, since no cable is used, it is possible to eliminate leakage of current. Also, motion in water is never interrupted. However, water is liable to be introduced into the transmitter 7, and in such a case an accurate electrocardiograph cannot be obtained.

SUMMARY OF THE INVENTION

This invention has been intended in light of the above problems.

An object of the invention is to solve the above problems by the provision of a water-proof device for a transmitter, which comprises a plurality of water-proof electrodes attached to the surface of a man for deriving minute current from the man, leads led out from the respective water-proof electrodes, a water-proof plug penetrated by a plurality of leads and formed on the outer periphery with an annular groove, a connector for connecting the leads extending from the water-proof plug, a transmitter to which the connector is connected, and a water-proof sack. The transmitter with the connector connected thereto is accommodated in the water-proof sack; the sack being sealedly secured to the water-proof plug by fitting an elastic band in the annular groove.

DETAILED DESCRIPTION OF THE PREFERRED EMBODIMENT

Now, the constitution and operation of the device according to the invention will be described in conjunction with a specific embodiment thereof with reference to the drawings.

Figure 1:
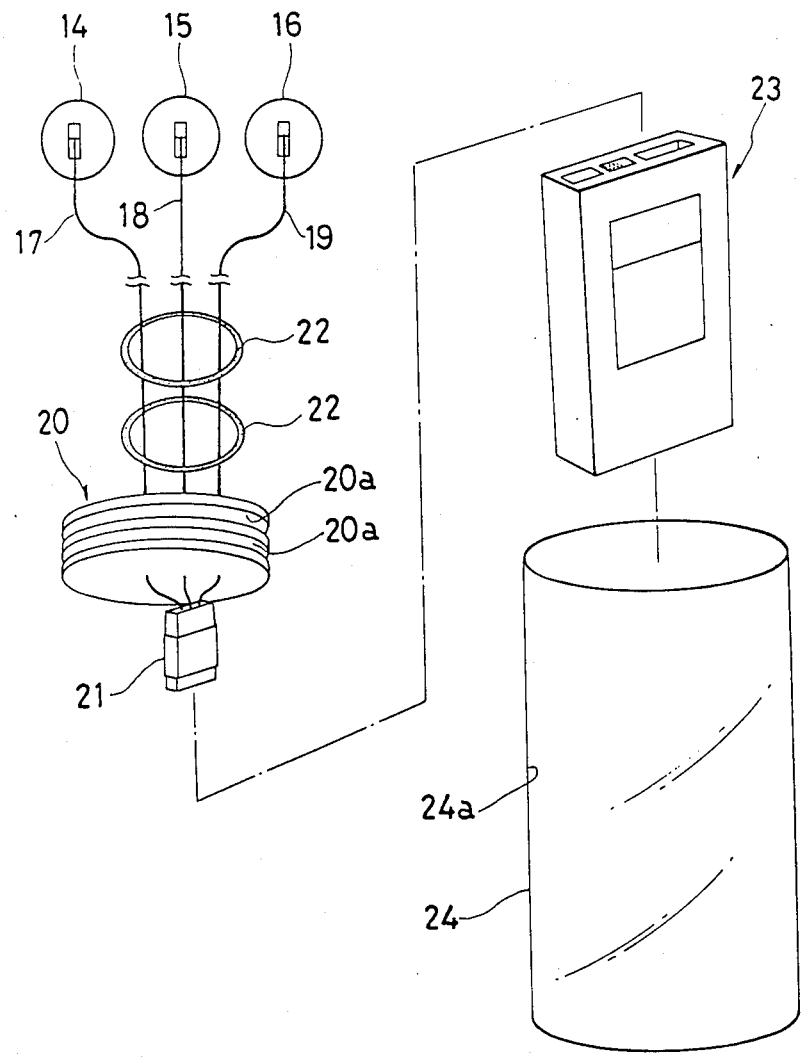
FIG. 1 is an exploded perspective view showing a water-proof device.

FIG. 1 is an exploded perspective view of an embodiment of the water-proof device of the transmitter according to the invention. Referring to the figure, reference numerals 14 to 16 designate water-proof electrodes, which are attached to the skin of a man for deriving minute current in the man.

The water-proof electrodes 14 to 16 are connected through leads 17 to 19 penetratng an elliptical water-proof plug 20 to a connector 21.

The elliptical water-proof plug 20 is made of synthetic rubber. Its outer periphery is formed with two axially arranged engagement grooves 20a. The engagement grooves 20a are adapted to receive endless elastic bands 22 made of rubber.

Reference numeral 23 designates a transmitter, to which is connected the end of the connector 21 other than the end to which the leads 17 to 19 are connected.

An electrocardiographic signal derived from a man by the water-proof leads 17 to 19 is led through the leads 17 to 19 to the transmitter 23 to be transmitted from the same.

Reference numeral 24 designates a water-proof sack made of rubber. The sack 24 has such a size that it can accommodate the transmitter 23 with redundancy.

Figure 2:
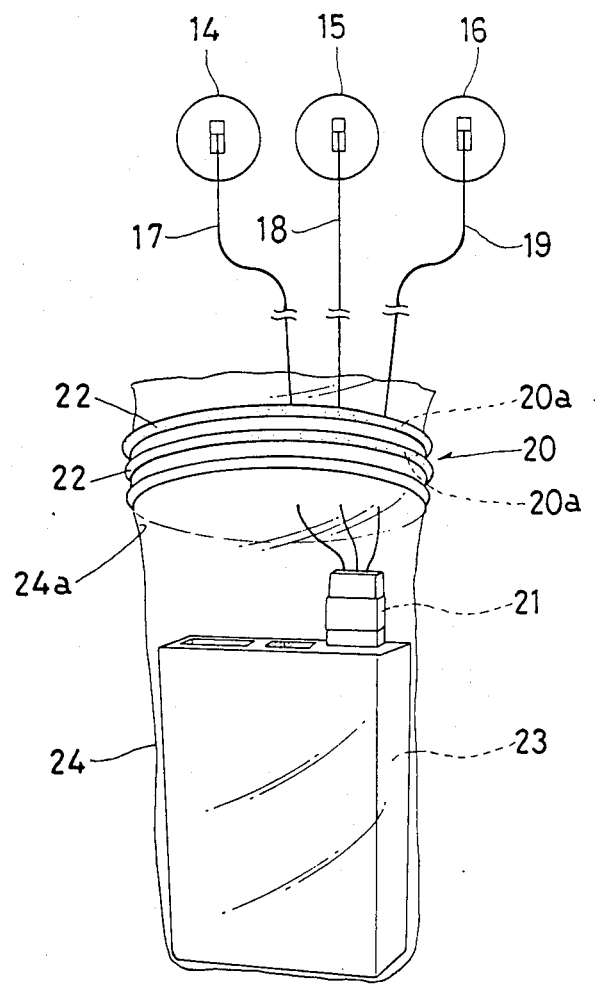
FIG. 2 is a view for explaining a water-proof state of the transmitter.
Figure 3:
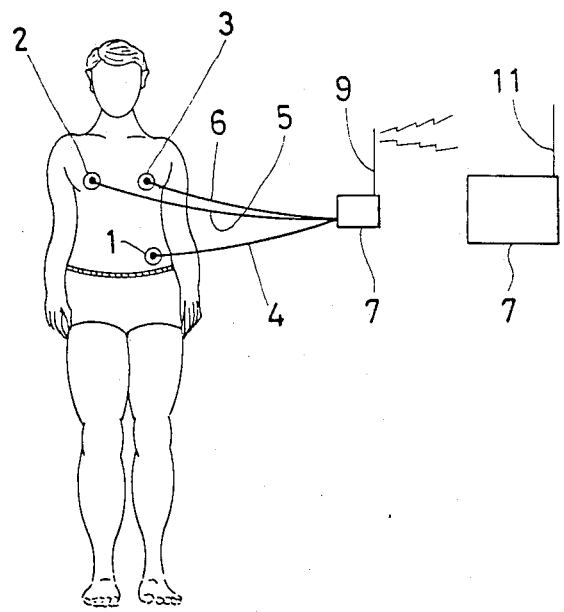
FIG. 3 is a view for explaining a method of receiving an electrocardiographic signal by radio under remote control.
Figure 4:
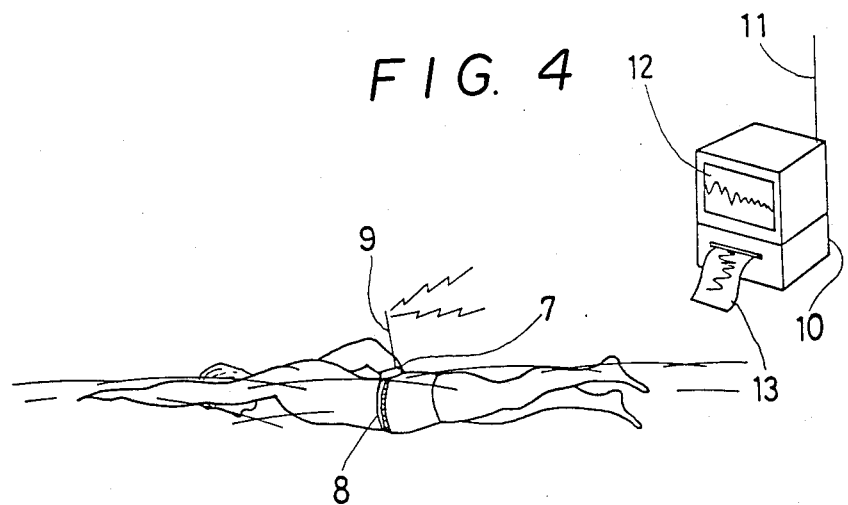
FIG. 4 is a view for explaining the recording of an electrocardiogram according to the electrocardiogram received by radio under remote control.

As shown in FIG. 2, the transmitter 23 with the connector 21 connected thereto is accommodated in the sack 24. Then, the inner wall 24a of the water-proof sack 24 is fitted on the outer periphery of the water-proof plug 20 to cover the engagement grooves 20a formed in the outer periphery of the water-proof plug 20. Subsequently, the endless elastic rubber bands 22 are fitted in engagement grooves 20a from above the water-proof sack 24, thereby closing the sack 24 to seal the transmitter 23 therein.

In the above way, the transmitter 23 is accommodated in the water-proof sack 24 in a perfectly water-proof state.

When a man swims with the transmitter 23 accommodated in the sack 24 mounted on him, the transmitter 23 is held water-proof, and no water will enter the transmitter 23.

As has been described in the foregoing, according to the invention the transmitter is accommodated in the water-proof sack, which is then sealed water-tight on the water-proof plug with the elastic bands fitted in engagement grooves formed in the outer periphery of the water-proof plug. Thus, the transmitter is held in a perfectly water-proof state to permit recording of an accurate electrocardiogram of a man in water.

What is claimed is:

1. A water-proof device for a transmitter comprising a plurality of water-proof electrodes attached to the surface of a man for deriving minute current from the man, leads led out from said respective water-proof electrodes, a water-proof plug penetrated by a plurality of leads and formed on the outer periphery with an annular groove, a connector for connecting said leads extending from said water-proof plug, a transmitter, to which said connector is connected, and a water-proof sack, said transmitter with said connector connected thereto being accommodated in said water-proof sack, said sack being sealedly secured to said water-proof plug by fitting an elastic band in said annular groove.

* * * * *

UNITED STATES PATENT AND TRADEMARK OFFICE
CERTIFICATE OF CORRECTION

PATENT NO. : 4,773,427
DATED : September 27, 1988
INVENTOR(S) : Hirokatsu Inoue, et al.

It is certified that error appears in the above-identified patent and that said Letters Patent is hereby corrected as shown below:

Title page:

In the Abstract, line 5, delete the comma "," and delete "for".

In the Abstract, line 6, delete the comma.

Column 1, line 20, after "heart" insert --examinations--.

Column 3, line 4, change "penetratng" to --penetrating--.

Signed and Sealed this

Twenty-first Day of February, 1989

Attest:

DONALD J. QUIGG

*Attesting Officer*  *Commissioner of Patents and Trademarks*